(12) United States Patent
Makino et al.

(10) Patent No.: US 6,346,179 B1
(45) Date of Patent: Feb. 12, 2002

(54) GAS SENSOR (75) Inventors: Keisuke Makino, Gifu; Shinya Awano, Aichi; Mitsunori Oi, Aichi; Takashi Nakao, Aichi; Teppei Okawa, Aichi, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/368,953

(22) Filed: Aug. 5, 1999

(30) Foreign Application Priority Data

Aug. 5, 1998 (JP) .......................... 10-222116
Jul. 23, 1999 (JP) .......................... 11-208925

(51) Int. Cl.$^7$ .......................... G01N 27/407
(52) U.S. Cl. .................. 204/428; 204/426
(58) Field of Search ................ 204/421–429

(56) References Cited

U.S. PATENT DOCUMENTS

| | | | |
|---|---|---|---|
| 4,559,126 A | * 12/1985 | Mase et al. ............ | 204/426 |
| 4,597,850 A | 7/1986 | Takahasi et al. | |
| 4,624,770 A | 11/1986 | Yamada et al. | |
| 4,916,934 A | 4/1990 | Nagata et al. | |
| 5,238,552 A | 8/1993 | Kato et al. | |
| 5,707,504 A | 1/1998 | Jyouno et al. | |
| 5,711,863 A | 1/1998 | Henkelmann et al. ...... | 204/428 |
| 5,800,689 A | * 9/1998 | Hori et al. ............ | 204/428 |
| 5,821,401 A | 10/1998 | Awarzamani et al. | |
| 5,880,353 A | 3/1999 | Graser et al. ............ | 73/23.2 |
| 5,948,963 A | 9/1999 | Kato et al. | |

FOREIGN PATENT DOCUMENTS

| | | | |
|---|---|---|---|
| DE | 35 22 867 A1 | 1/1986 | |
| DE | 38 43 089 A1 | 7/1989 | |
| DE | 90 14 826 U | 4/1992 | |
| DE | 42 20 726 A1 | 1/1993 | |
| EP | 0 837 324 A2 | 4/1988 | |
| EP | 0 458 368 A2 | 11/1991 | |
| EP | 0 822 410 A2 | 2/1998 | |
| GB | 2 312 516 A | 10/1997 | |
| JP | 63-54061 | 4/1988 | .......... G01N/27/12 |
| JP | 1-30103 | 6/1989 | .......... G01N/27/58 |
| JP | 10-253576 A | 9/1998 | |
| JP | 10-282042 A | 10/1998 | |
| JP | 10-318980 A | 12/1998 | |
| JP | 11-108884 A | 4/1999 | |

* cited by examiner

*Primary Examiner*—T. Tung
(74) *Attorney, Agent, or Firm*—Sughrue Mion, PLLC (57) ABSTRACT

A gas sensor including a detection element having a front-end portion, a detection portion formed at the front-end portion of the detection element, and a protector that covers the detection portion. The protector includes a first portion having a first sidewall and a second portion having a second sidewall disposed outside the first portion. The first sidewall has an axial front end and a tapering portion. The tapering portion is formed from the axial front end of the first sidewall. The side portion has a front-end surface provided with a first gas outlet, and the second portion has a front-end surface provided with a second gas outlet. Furthermore, at least one gas inlet is formed to the sidewall of the second portion opposite the tapering portion, and plural gas inlets are formed on the sidewall of the first portion.

20 Claims, 9 Drawing Sheets

GAS SENSOR

BACKGROUND OF THE INVENTION

1. Field of the Invention

The present invention relates to a gas sensor, such as an oxygen sensor, an HC sensor, or an $NO_x$ sensor, for detecting a component of a gas to be measured.

2. Description of the Related Art

A known gas sensor of the type described above has a rodlike or cylindrical detection element having a detection portion for detecting a component of interest. The detection portion is formed at the front end of the detection element, which is housed in a metallic casing. This gas sensor has a protector that covers the detection portion placed within an environment to be measured. Gas passage holes are formed in the sidewall of the protector. A gas such as exhaust gas to be measured is guided into the protector via the gas passage holes and brought into contact with the detection portion.

Many of various gas sensors recently developed for use in automobiles use a double-structure protector consisting of inner and outer cylindrical portions to provide enhanced protection for the detection portion from water droplets, oil droplets, and contaminants. The conventional double-structure protector indicated by 106 in FIG. 9 has the inner and outer cylindrical portions 106a and 106b. Gas inlets 163 and 161 are formed in the sidewalls of the cylindrical portions, respectively. Gas under measurement first passes through the gas inlets 163 in the outer cylindrical portion 106a and then passes through the gas inlets 161 in the inner cylindrical portion 106b to the detection portion 102.

In the protector of the double structure described above, the protecting performance of the detection portion is enhanced. However, the resistance to the passing gag is increased because of the double wall structure. For example, the rate at which the gas under measurement is exchanged is often low in the space between the outside and inside of the protector. Therefore, the structure has the problem that the response tends to be delayed if the concentration of the component under measurement within the measured ambient varies rapidly.

Figure 9:
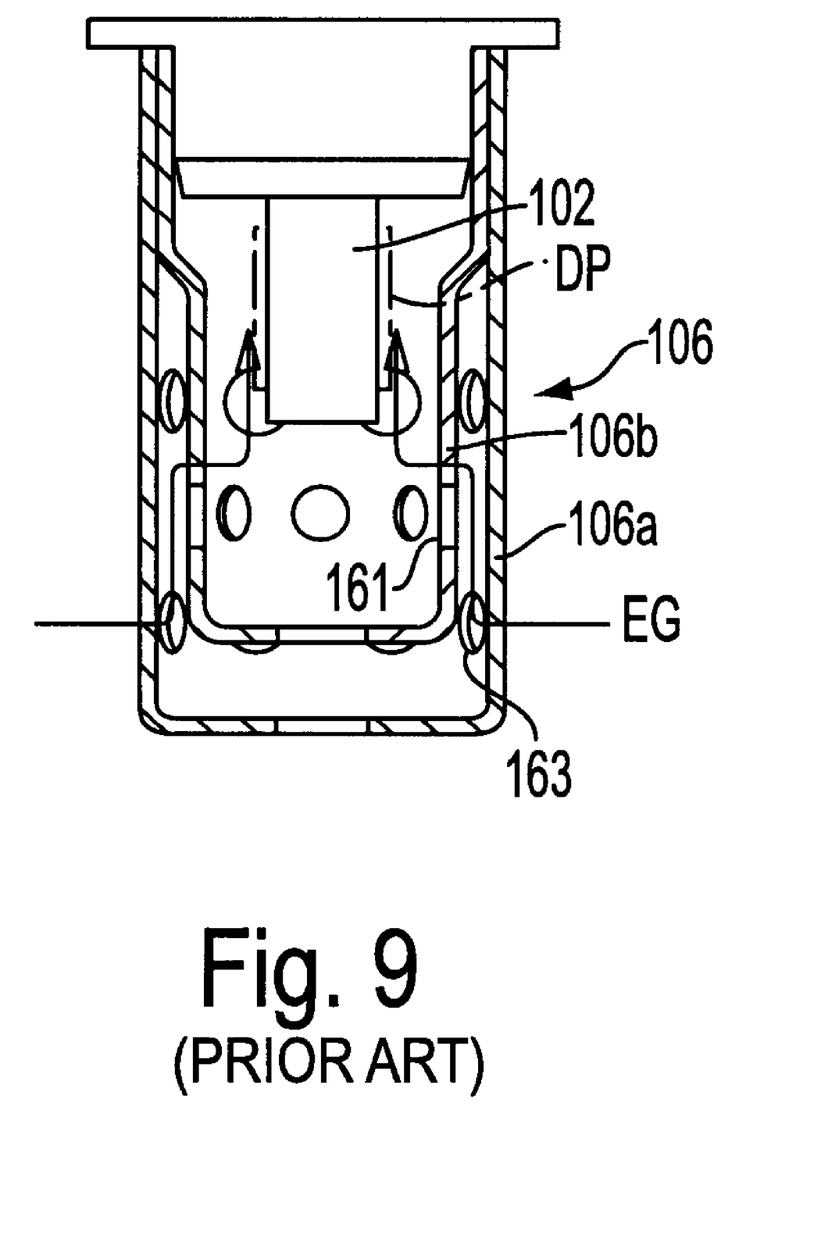
FIG. 9 is a cross-sectional view showing the structure of a prior art protector.

If the detection portion 102 shown in FIG. 9 has a gas-sensitive surface DP on only one side of a lamination, the following problem takes place. If gas EG to be measured such as exhaust gas flows into the protector 106 from the side of the gas-sensitive surface DP, the gas stream arrives at the gas-sensitive surface DP relatively directly. Therefore, where the concentration of the component under measurement changes, the detection response is relatively good. However, where the gas flows from the opposite side, the gas stream strikes the surface of the detection portion 102 on the opposite side of the sensitive surface DP. This tends to delay the response of the detection. In this way, the sensor has the drawback that the response and output characteristics are easily affected according to the direction of the gas stream to be measured relative to the protector.

If the protector is built as a single structure, the rate at which the gas is exchanged between the inside and outside of the protector is enhanced so that the response of the sensor is improved. Of course, however, the function of protecting the detection portion deteriorates. If the gas flow rate increases rapidly, or if the gas temperature drops quickly, the temperature of the detection portion drops, thus deactivating an oxygen concentration cell (also known as a differential aeration cell). This leads to a deterioration of the detection sensitivity, or the output signal from the cell is interrupted. The gas exchange rate may also be increased by increasing the dimensions of the gas inlets in the double-structure protector. This structure inevitably produces problems similar to those with the aforementioned single-structure protector, though the results may be more or less serious. Hence, it has been difficult to achieve good response and high protecting performance simultaneously.

SUMMARY OF THE INVENTION

It is therefore an object of the present invention to provide a gas sensor which is provided with a multiple-structure protector and thus protects a detection element well and which has sensor response characteristics depending to a lesser extent on the direction of the stream of a gas under measurement than conventional and, therefore, produces uniform response or output characteristics at an appropriate level.

The above object of the present invention has been achieved by providing a gas sensor which comprises a detection element having a front-end portion, a detection portion formed on or in the front-end portion of the detection element, and a protector that covers the detection portion. The protector comprises a first cylindrical portion and a second cylindrical portion disposed outside said first cylindrical portion. A tapering reduced portion is formed at an axially front-end side of a sidewall portion of said first cylindrical portion. A second side gas inlet is formed in a sidewall portion of said second cylindrical portion and corresponds in position to said reduced portion.

In the above-described gas sensor in accordance with the present invention, the protector is of the multiple structure, i.e., at least the double structure having the inner first cylindrical portion and the outer second cylindrical portion. This suppresses intrusion of water droplets, oil droplets, and so on into the protector. Hence, the instrument is excellent in protecting the detection portion.

Furthermore, a tapering reduced portion is formed at an axially front side of the sidewall portion of the first cylindrical portion. Second side gas inlets are formed in the sidewall portion of the second cylindrical portion and correspond in position to the reduced portion. Gas stream to be measured strikes the reduced portion and flows along the outer surface of the sidewall portion of the reduced portion. This produces a negative pressure at the side of the first side gas outlet, decreasing the pressure inside the first cylindrical portion. The gas under measurement is quickly drawn in from the first gas inlets spaced circumferentially. In consequence, sufficient response can be secured in spite of the multiple structure of the protector.

Where the first cylindrical portion is cut along a plane including the axis, the cross section through the tapering portion may be straight or curved outwardly or inwardly. Setting the diameter of the front end of the reduced portion smaller than that of the base end is preferable for production of a negative pressure in the first side gas outlet.

More specifically, the first cylindrical portion has the tapering portion that is a truncated cone coupled to the front end of a cylindrical body. For example, once the total length of the first cylindrical portion is set, the tilt angle of the outer surface of the tapering portion can be easily adjusted to a value adapted for production of a negative pressure in the first side gas outlet by adjusting the length of the cylindrical body formed at the side of the base end.

Accordingly, a specific embodiment of the present invention comprises:

a detection element for detecting a detected constituent of a gas under measurement by a detection portion formed in a front-end portion;

a cylindrical element container that covers the detection element while permitting the detection portion to protrude; and a protector coupled to an opening end portion in the element container through which the detection portion protrudes, the protector covering the detection portion while permitting passage of the gas to be measured;

said protector comprising a first cylindrical portion circumferentially surrounding the detection portion around the axis of the detection element, the first cylindrical portion having a sidewall portion provided with plural first side gas inlets circumferentially spaced from each other at regular intervals, a tapering reduced portion being formed at an axially front end side of the sidewall portion, the reduced portion having a front-end surface provided with a first gas outlet, and a second cylindrical portion having an opening portion at its front end and located outside the first cylindrical portion such that a given gap is formed between the first and second cylindrical portions, the second cylindrical portion permitting the gas under measurement to flow along the tapering outer surface of the reduced portion from its base end toward the front end and inhibiting the gas under measurement from directly flowing into the first side gas inlets in a direction perpendicular to the axis of the first cylindrical portion where the second cylindrical portion is placed within the gas stream under measurement, said reduced portion of said first cylindrical portion protruding from the opening portion in the second cylindrical portion in such a way that the first side gas outlet is located closer to the base end than the front-end surface of the second cylindrical portion in the direction of the axis or that inner fringes of the opening portion in the second cylindrical portion are located opposite to the outer surface of the reduced portion.

The detection portion described above can be fabricated as an oxygen detection portion comprising an oxygen concentration cell and a planar heater. The oxygen concentration cell is built by forming a first porous electrode at one side of a board-like layer of an oxygen ion conductive solid electrolyte and a second porous electrode at the opposite side. The first porous electrode forms a detection electrode. The second electrode forms a reference oxygen electrode. The planar heater is formed on the reference oxygen-side porous electrode. The electrode surface of the detection-side porous electrode forms a gas-sensitive surface. This structure can be preferably used in a λ-type oxygen sensor, for example.

The above-described gas sensor in accordance with the present invention has the first cylindrical portion having the sidewall portion provided with plural first side gas inlets circumferentially spaced from each other at regular intervals. The first side gas inlets are formed by two sets of holes axially spaced from each other. The holes of one of the two sets are formed so as to be located opposite to the detection portion. The holes of the other set are located closer to the front end than the front end of the detection portion. For example, if the first side gas inlets consist of only one array of holes corresponding to the detection portion, and if a negative pressure increases the rate at which the gas under measurement flows into the first cylindrical portion, a major part of the entering gas will strike the detection portion. If the gas contains water droplets or the like, the water droplets strike the detection portion, impairing the protecting function of the protector. Accordingly, if one or more arrays of holes are added ahead of the front end of the detection element, the flow of the water droplets is dispersed and, therefore, the protecting function can be maintained.

The second cylindrical portion permits the gas under measurement to flow along the outer surface of the tapering portion at the front end of the first cylindrical portion from its base end toward the front end. This stream of gas develops a negative pressure in the first side gas outlet formed at the front end of the tapering portion. Thus, the interior of the first cylindrical portion is evacuated. Consequently, the gas under measurement is drawn into the first cylindrical portion almost isotropically from the peripherally spaced first gas inlets. As a result, uniform response or output can be obtained, irrespective of the angle at which the gas stream strikes the surface of the detection portion from around the axis of the protector, i.e., regardless of the direction of the gas stream. This is especially advantageous where a gas-sensitive surface is formed in a part of the peripheral outer surface of the detection portion or where a gas-sensitive surface in the form of a planar, thin or thick film is formed at one side.

Another gas sensor in accordance with the present invention has the first cylindrical portion having a front-end surface provided with a first side gas outlet. A second side gas outlet is formed in a front-end surface of the second cylindrical portion. The second side gas outlet is located closer to the front end than the first side gas outlet. In this configuration, the measured gas introduced from the second side gas inlets directly collides against the tapering portion, increasing the flow velocity of the gas along the tapering portion. Hence, the negative pressure produced in the first side gas outlet can be increased. As a result, the rate at which the measured gas is drawn in from the first side gas inlets is increased. Thus, the rate at which the measured gas is exchanged within the first cylindrical portion is increased. Consequently, the detection response or the response of the output to concentration variations is improved further.

To make effective use of the sucking effect described above, the second side gas outlet in the gas sensor in accordance with the present invention can be made larger than the first side gas outlet. In this configuration, outflow of the gas under measurement from the second side gas outlet is not hindered and thus smooth. Variations in the negative pressure produced in the first side gas outlet can be suppressed. Consequently, stable detection response or output response to concentration variations can be obtained.

The first and second side gas outlets can be formed coaxially with each other. In this configuration, the measured gas drawn in from the first cylindrical portion via the first side gas outlets can be smoothly expelled from the second side gas outlets, together with the gas flowing along the tapering portion. This can further improve the detection response of the sensor or the output response to variations in the concentration.

A further gas sensor in accordance with the present invention has the first cylindrical portion having a front-end surface provided with the first side gas outlet and the second cylindrical portion having a front-end surface provided with the second side gas outlet. The first side gas outlet can be located closer to the front-end side than the second side gas outlet. In this configuration, the second side gas outlet directly faces the reduced portion of the front-end side of the first cylindrical portion. If the gap between the outer surface of the reduced portion and the inner fringes of the second side gas outlet is narrowed, the flow velocity of the gas under measurement along the reduced portion is increased further. The negative pressure produced in the first side gas outlet can be increased further. Accordingly, this further increases the rate at which the gas under measurement inside the first cylindrical portion is exchanged. The detection response or the output response to concentration variations can be improved further.

In still another gas sensor in accordance with the present invention, the second side gas inlets are formed as follows. Breaks are formed in the sidewall portion of the second cylindrical portion such that the breaks have direction change portions that change direction from one base end portion and go to the other base end portion. Claw-like portions surrounded by the breaks are bent radially inwardly, thus forming the second side gas inlets. In this configuration, the claw-like portions overlap the second side gas inlets like flaps. This suppresses intrusion of water droplets, oil droplets, and so on into the protector. This further improves the protection of the detection portion. Furthermore, the flow of the gas under measurement is made to circulate along the sidewall portion of the second cylindrical portion by the claw-like portions bent radially inwardly. In consequence, the flow velocity of the gas along the reduced portion is increased. The negative pressure produced in the first side gas outlet can be increased further. As a result, the rate at which the gas under measurement inside the first cylindrical portion is exchanged is enhanced. Hence, the detection response or output response to concentration variations can be improved further.

In yet another gas sensor in accordance with the present invention, the holes of the set located opposite to the detection portion form breaks in the sidewall portion of the first cylindrical portion. The breaks have direction change portions that change direction from one base end portion and go to the other base end portion. Claw-like portions surrounded by the breaks are bent radially inwardly. In this structure, the claw-like portions overlap the first side gas inlets like flaps. This suppresses intrusion of water droplets, oil droplets, and so on into the first cylindrical portion. This enhances the protection of the detection portion. Furthermore, the flow of the gas under measurement is made to circulate along the sidewall portion of the first cylindrical portion by the claw-like portions bent radially inwardly. The gas is sucked almost isotropically. As a result, the gas under measurement makes uniform circulating flow around the axis of the protector. Uniform response or output can be obtained.

Other objects and features of the invention will appear in the course of the description thereof, which follows.

BRIEF DESCRIPTION OF THE DRAWINGS

FIG. 1(*a*) is a front elevation and FIG. 1(*b*) is a vertical cross section of an oxygen sensor as an example of a gas sensor in accordance with the present invention;

FIG. 2(*a*) is an exploded perspective view of a ceramic element acting as a detection element in the oxygen sensor shown in FIGS. 1(*a*) and 1(*b*);

FIG. 2(*b*) is a vertical cross section of the detection element shown in FIG. 2(*a*);

FIGS. 2(*c*) and 2(*d*) are vertical cross sections of parts of the detection element shown in FIG. 2(*b*);

FIG. 3(*a*) is a fragmentary vertical cross section of the protector shown in FIGS. 1(*a*) and 1(*b*) and FIG. 3(*b*) is a cross-sectional view taken on line A—A;

FIG. 4(*a*) is a fragmentary vertical cross section of the protector shown in FIGS. 1(*a*) and 1(*b*), illustrating the dimensions of various portions of the protector, and FIG. 4(*b*) is a cross-sectional view of the protector;

FIG. 5(*a*) is a fragmentary vertical cross section illustrating the operation of the protector shown in FIGS. 1(*a*) and 1(*b*), and FIG. 5(*b*) is a cross section taken on line B—B;

FIGS. 6(*a*)–6(*d*) are vertical cross sections of modifications of the protector shown in FIGS. 1(*a*) and 1(*b*);

FIGS. 7(*a*)–7(*c*) and 7(*e*)–7(*g*) are vertical cross sections of further modifications of the protector shown in FIGS. 1(*a*) and 1(*b*);

FIG. 7(*d*) is a cross section of the protector shown in FIGS. 1(*a*) and 1(*b*); and FIG. 8(*a*) is a fragmentary vertical cross section of a still another modification of the protector, FIG. 8(*b*) is a cross section taken on axis C—C, FIG. 8(*c*) is a cross section taken on axis D—D, and FIG. 8(*d*) is an enlarged front plan view of the modification.

DESCRIPTION OF THE PREFERRED EMBODIMENTS

Hereunder, a mode for carrying out the invention is described with reference to the embodiments shown in the drawings.

Figure 1A:
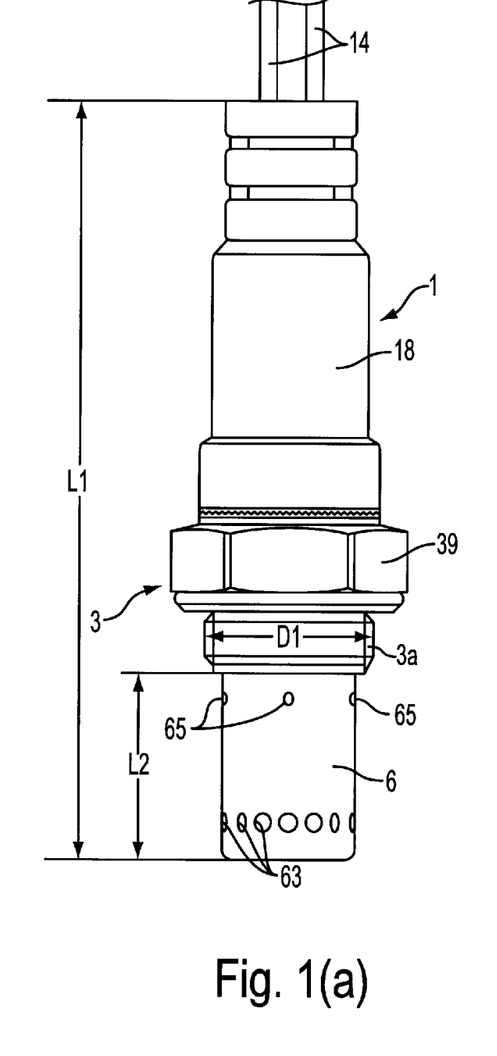
Figure 1B:
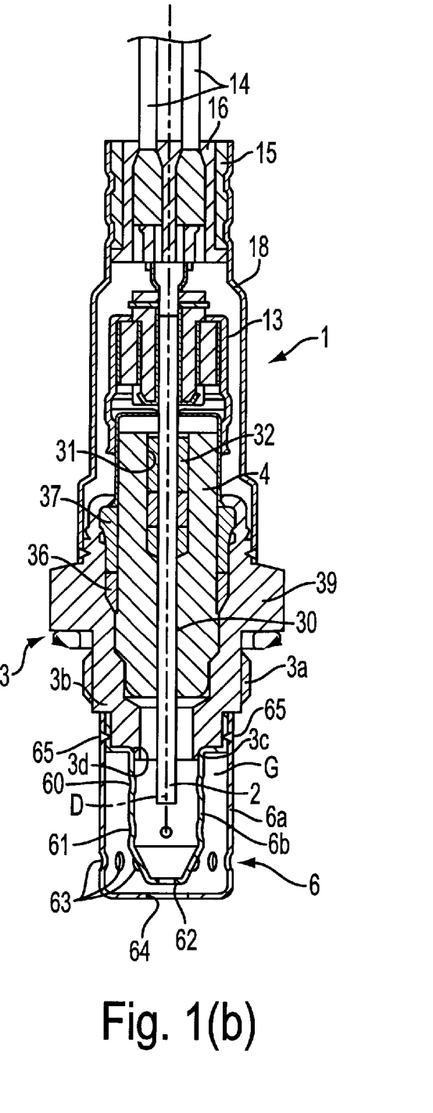

Referring to FIGS. 1(*a*) and 1(*b*), there is shown in oxygen sensor 1 that is one example of a gas sensor in accordance with the present invention. This oxygen sensor 1 detects the oxygen concentration of exhaust gas emitted from an automobile or the like. This oxygen sensor is normally known as a λ-type oxygen sensor and comprises a ceramic detection element 2 in the form of a planar, thin or thick film. This element 2 is mounted to a main metal fitting 3. A threaded portion 3*a* for mounting is formed on the outer surface of the fitting 3. A detection portion D formed at a side of the front end is mounted by the threaded portion 3*a* within the exhaust pipe of an automobile. The detection portion D is exposed to the high-temperature exhaust gas flowing through the exhaust pipe. This exhaust gas is a gas to be measured.

Figure 2A:
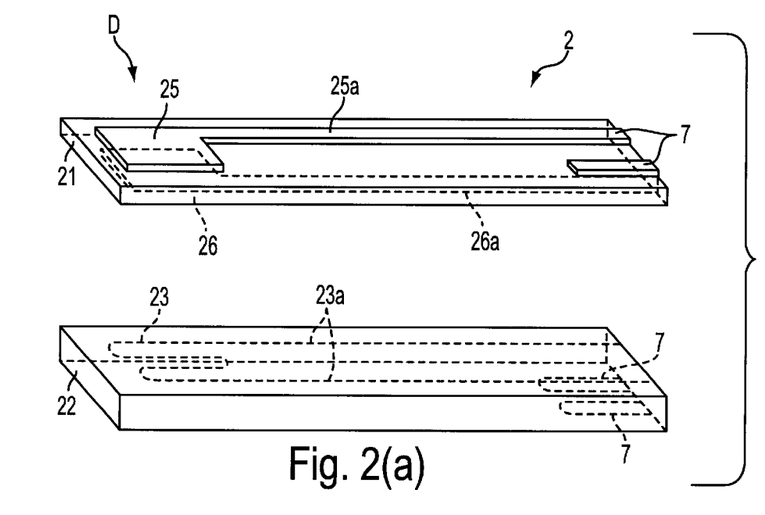

The ceramic element 2 is rectangular in a cross section taken across the axis. As shown in FIG. 2(*a*), the ceramic detection element 2 comprises a heater 22 and a horizontally elongated oxygen concentration cell 21 mounted n the heater 22. This heater 22 acs to heat the oxygen concentration cell 21 to its given activation temperature. The cell 21 is made of an oxygen ion conductive solid electrolyte consisting mainly of zirconia or the like. The heater 22 is a well-known ceramic heater.

The oxygen concentration cell 21 has porous electrodes 25 and 26. Leads 25*a* and 26*a* are coupled to the electrodes 25 and 26, respectively, and extend longitudinally of the porous electrodes 25 and 26 toward the base end of the oxygen sensor 1 at which the sensor is mounted. The lead 25*a* extending from the electrode 25 which is not opposite to the heater 22 and has an electrode terminal 7 at its end.

As shown in FIG. 2(*c*), a via hole 26*b* extends across the thickness of the oxygen concentration cell 21. The lead 26*a* extending from the electrode 26 which is opposite to the heater 22 is connected with an electrode terminal 7 formed on the opposite side through the via hole 26*b*. That is, the electrode terminals 7 of the porous electrodes 25 and 26, respectively, are arranged side by side at one end of the surface of the electrode 25. The above-described electrodes, electrode terminals, and the via hole are obtained by preparing a paste of a metal powder, such as a Pt or Pt-alloy, having catalytic activity inducing an oxygen molecule dissociation reaction, screen printing a pattern with the paste, and sintering the paste.

Figure 2B:
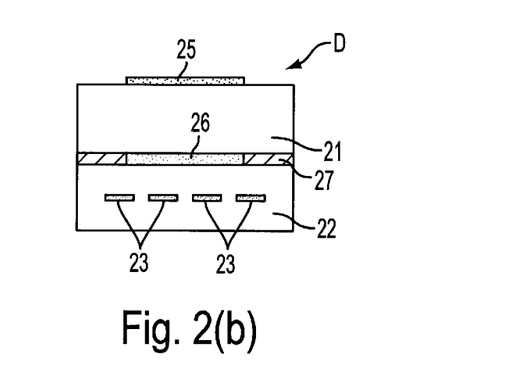
Figure 2C:
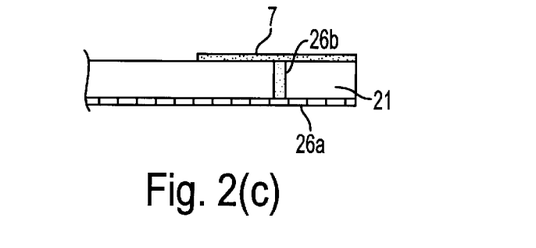
Figure 2D:
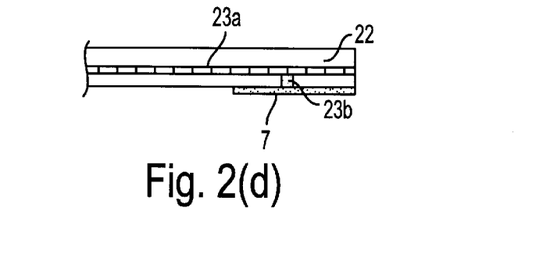

Other electrode terminals 7 are formed at one end of the surface of the heater 22 not opposite to the oxygen concentration cell 21. Leads 23a for energizing a resistive heat-generating pattern 23 forming the heater 22 are connected with these electrode terminals 7, respectively, through via holes 23b, as shown in FIG. 2(d). The heater 22 is bonded to the oxygen concentration cell 21 via a layer 27 of $ZrO_2$-based or $Al_2O_3$-based ceramic, as shown in FIG. 2(b). A very weak pumping current is applied to the bonded porous electrode 26 (on the oxygen reference side) of the cell 21, so that this electrode 26 acts as an oxygen reference electrode. The opposite porous electrode 25 serves as a detection electrode that comes into contact with exhaust gas, and the surface of the electrode 25 acts as a gas-sensitive surface.

Referring back to FIGS. 1(a) and 1(b), the ceramic element 2 is inserted in a hole 30 formed in an insulator 4 located inside the main metal fitting 3. The ceramic element 2 is fixedly mounted inside the insulator 4 such that the detection portion D at the front end protrudes from the front end of the main metal fitting 3 firmly secured to the exhaust pipe. A large space 31 is formed in the insulator 4 and has a horizontal cross section larger than that of the hole 30. One end of the space 31 is in communication with the rear end of the hole 30, while the other end opens to the rear end surface of the insulator 4. The inner surface of the space 31 and the outer surface of the ceramic element 2 are sealed together by a layer 32 of a sealing material consisting mainly of a glass, such as crystallized zinc-borosilicate glass.

A talc ring 36 and a crimping ring 37 are adjacent to each other in the axial direction and fitted between the insulator 4 and the main metal fitting 3. The main metal fitting 3 is mounted to the insulator 4 by crimping the outer surface of the rear end of the main metal fitting 3 against the insulator 4 via the crimping ring 37. The side of the protruding portion of the detection portion D in the direction of the axis of the main metal fitting 3 is referred to as the front side herein. The opposite side is referred to as the rear side.

A ceramic separator 16 and a grommet 15 are fitted inside the end (top in the page) of an outer cylinder 18. A connector 13 is mounted inside these separator 16 and grommet 15. The lead 14 has a rear-end portion extending outwardly through the ceramic separator 16. The lead 14 has a front-end portion electrically connected with the electrode terminals 7 (4 polarities) of the ceramic element 2 shown in FIG. 2(a) via the connector 13.

Figure 3A:
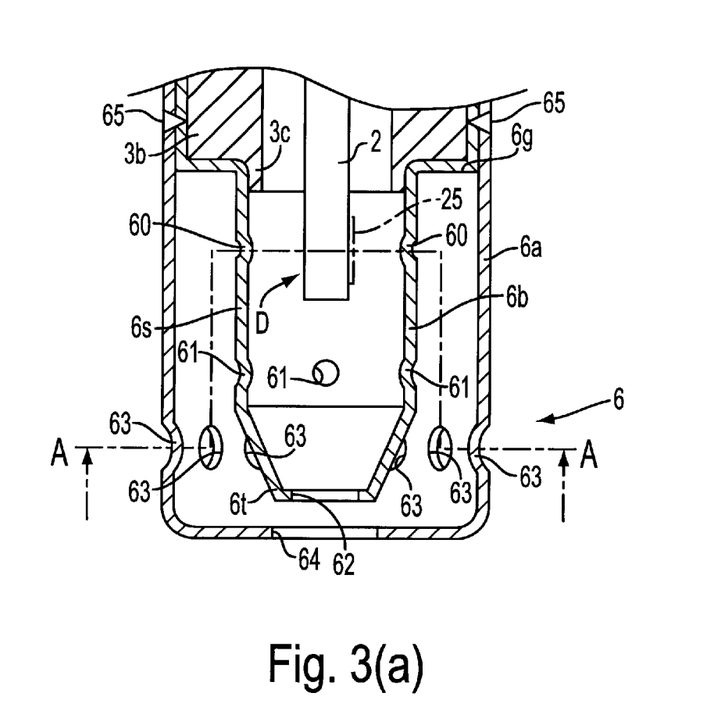
Figure 3B:
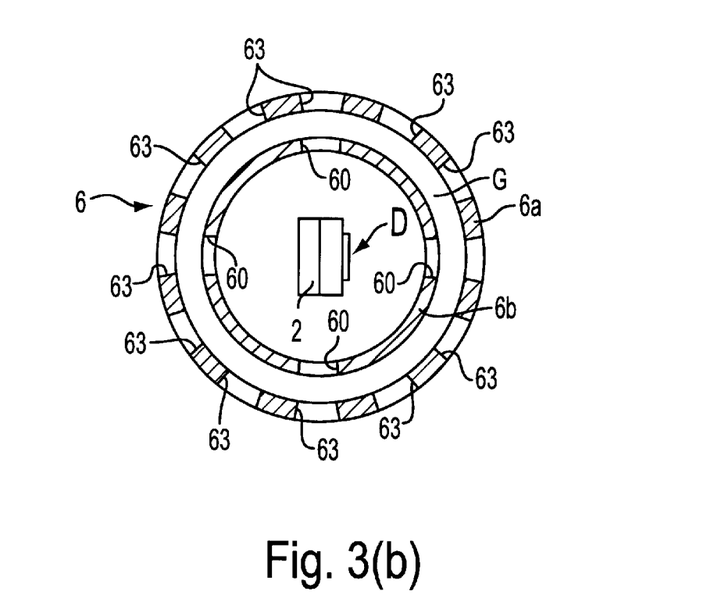

The protruding portion of the ceramic element 2, i.e., the protector 6 that covers the detection portion D, is mounted to the front end of the main fitting 3. The protector 6 has the double-structure, i.e., having the inner first cylindrical portion 6b and the outer second cylindrical portion 6a. As shown in FIGS. 3(a) and 3(b), the first cylindrical portion 6b surrounds the detection portion D around the axis of the detection element 2. First side gas inlets 60 and 61 are formed in the sidewall of the first cylindrical portion 6b and regularly spaced from each other circumferentially. A tapering portion 6t is formed on the side of the front end of the sidewall as viewed in the axial direction. A first side gas outlet 62 is formed in the front-end surface of the tapering portion 6t. In particular, the tapering portion 6t takes the form of a truncated cone coupled to the front end of a cylindrical body 6s. The first side gas inlets 60 and 61 include arrays of holes 60 and 61 almost substantially equally spaced from each other circumferentially of the body 6s. In the present embodiment, two arrays of circular holes 60 and 61 are formed in the direction of the axis of the body 6s, each array containing 4 holes.

Figure 5A:
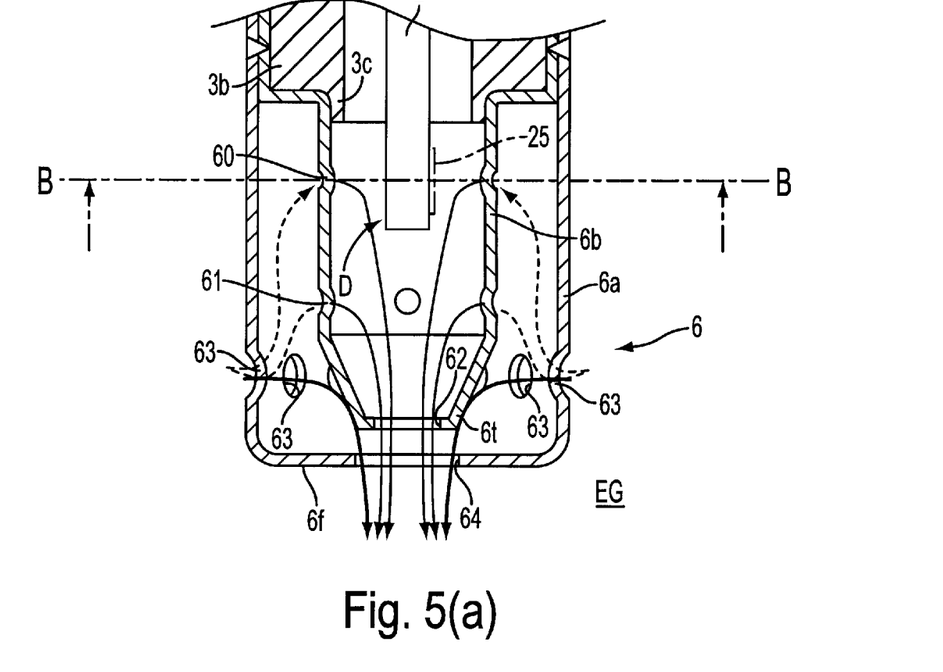
Figure 5B:
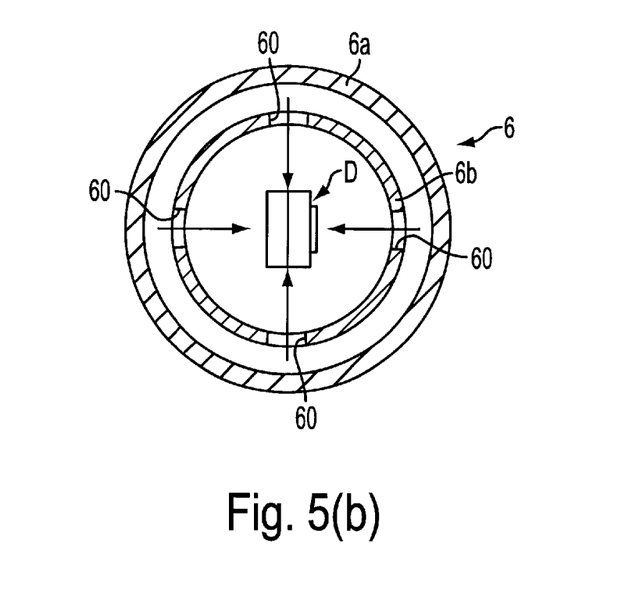

The second cylindrical portion 6a is located outside the first cylindrical portion 6b such that a given gap G is formed between them. The front end of the second cylindrical portion 6a protrudes beyond the first cylindrical portion 6b. A second side gas outlet 64 is formed in the front-end surface. Where the detection element 2 is placed within stream EG of gas under measurement that flows perpendicular to the axis of the detection element 2 as shown in FIG. 5(a), the gas EG introduced from the second side gas inlets 63 formed in the sidewall flows along the outer surface of the tapering portion 6t from the base end toward the front end and leaves from the second side gas outlet 64.

More specifically, the second cylindrical portion 6a is shaped cylindrically and has a bottom portion 6f at its front end. The second side gas inlets 63 (12 inlets in the present embodiment) are formed in positions closer to the front end of the sidewall corresponding to the tapering portion 6t. The second side gas inlets 63 are substantially regularly spaced from each other circumferentially. The second side gas outlet 64 is formed in a coaxial relation to the first side gas outlet 62 in the center of the bottom portion 6f. The second side gas inlet 63 is formed in an offset relation to the first side gas inlets 60 and 61 in the direction of the axes of the cylindrical portions 6a and 6b. The second cylindrical portion 6a prevents the gas EG under measurement from flowing directly into the first side gas inlets 60 and 61 in a direction perpendicular to the direction of the axes.

The two arrays of holes 60 and 61 form the first side gas inlets. One array 61 is located ahead of the front end of the detection portion in the direction of the axes. The other array 60 is located at the side of the base end. The stream of the gas under measurement may contain poisoning materials such as phosphor, sulfur, and silicon, in addition to water droplets formed by condensate water. These water droplets and poisoning materials pass into the first cylindrical portion 6b through the array of holes 60 or 61, if they are contained. However, those materials which enter from the hole array 61 are highly likely to be discharged to the outside while entrained by the gas stream. They are hardly deposited on the detection portion. That is, the first side gas inlets include the two arrays of holes 60 and 61 on opposite sides of the front end of the detection portion as described above. This improves the durability of the detection portion against the condensate water and poisoning materials.

Referring again to FIGS. 1(a) and 1(b), the main metal fitting 3 has a reduced portion 3b having a diameter slightly smaller than that of the mounting threaded portion 3a. The reduced portion 3b is located closer to the front end than the threaded portion 3a. A cylindrical positioning protruding portion 3c protrudes from the fringes of the opening on the front end surface of the reduced portion 3b, as shown in FIG. 3(a). The first cylindrical portion 6b is placed in position by the positioning protruding portion 3c, and an enlarged portion 6g formed at the side of the opening is fitted over the reduced portion 3b of the main metal fitting 3g. The second cylindrical portion 6a is fitted over the reduced portion 3b of the main metal fitting 3 from outside the enlarged portion 6g of the first cylindrical portion 6b in the opening on the side of the base end. The second cylindrical portion 6a and the enlarged portion 6g are welded to the reduced portion 3b at a circumferentially extending weldment 65 by spot welding, laser welding, or other method. Where spot welding is used, the weldment consists of spots spaced from each other. Where laser welding is utilized, the weldment is a continuous annular portion.

The oxygen sensor 1 is mounted to the automotive exhaust pipe by the mounting threaded portion 3a. If the detection portion D is exposed to exhaust gas EG, the porous electrode 25 (FIG. 2(a)) of the oxygen concentration cell 21 comes into contact with the exhaust gas EG, producing an electromotive force according to the oxygen concentration of the gas EG across the cell 21. This electromotive force is taken as the output from the sensor. Since the protector 6 has a double structure as described above, it is excellent in protecting the detection portion D. On the other hand, the exhaust gas EG introduced in the protector 6 from the second side gas inlets 63 flows along the outer surface of the tapering portion 6t of the first cylindrical portion 6b and goes from the side of the base end toward the frond end. Then, the gas flows out from the second side gas outlet 64, as shown in FIG. 5(a).

If such a gas stream is produced, a negative pressure is generated in the first side gas outlet 62, evacuating the inside of the first cylindrical portion 6b. The exhaust gas EG is drawn in from the circumferentially spaced first side gas inlets 60, 61 almost isotropically. As a result, if the gas EG is supplied to the detection portion D almost isotropically irrespective of the angle at which the gas stream under measurement strikes the detection portion surface around the axis of the protector. Therefore, uniform response or output characteristics can be obtained irrespective of the direction of the gas stream. Since a negative pressure is developed in the first side gas outlet 62, a relatively large amount of gas stream can be created along the surface (gas-sensitive surface) of the detection-side porous electrode 25 by the exhaust gas EG sucked from the first side gas inlets 60 and 61. In consequence, good output response can be derived if the ambient is varied from rich to lean. Furthermore, little difference in effect is produced, depending on the direction of the gas stream relative to the protector 6.

Figure 4A:
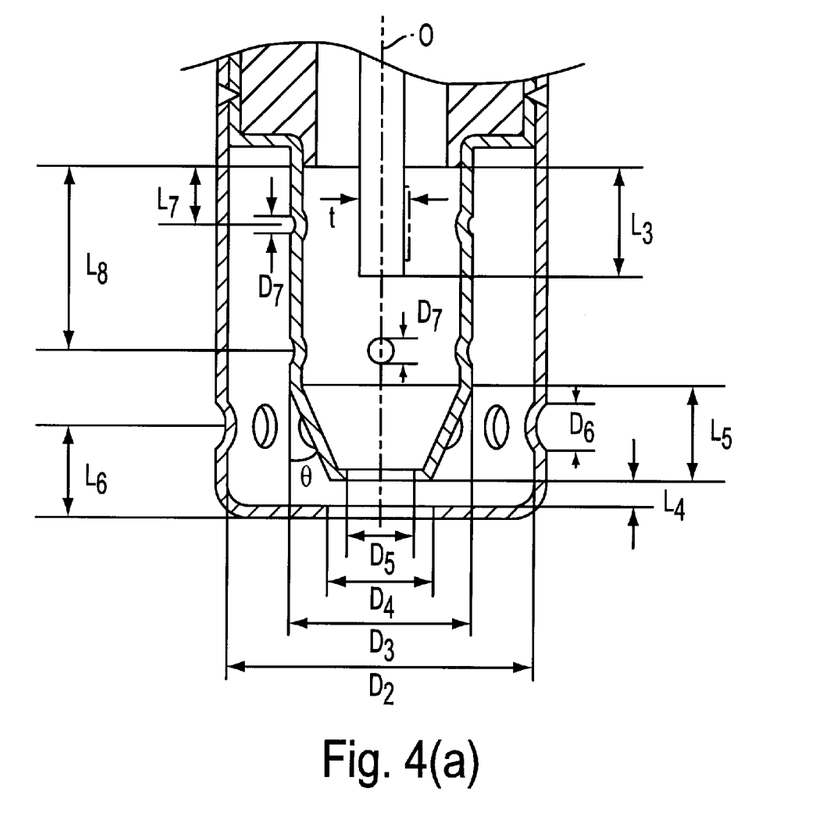
Figure 4B:
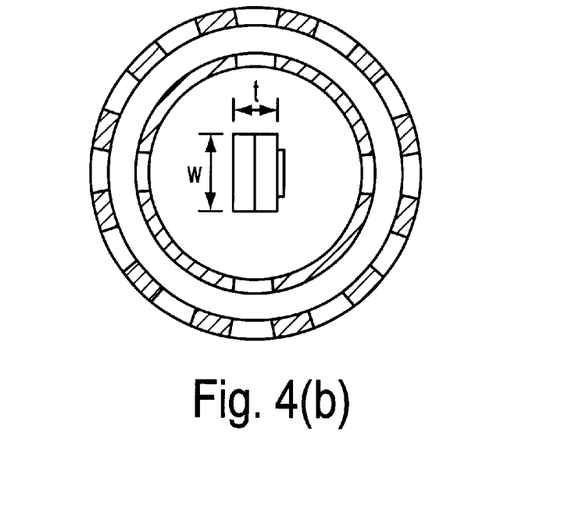

Examples of the dimensions of the various portions of the oxygen sensor 1 are described by referring to FIGS. 1 and 4. Where dimensions are given in ranges, specific examples of numerical values are presented in the parentheses. Like components are indicated by like reference numerals in both FIGS. 3(a)–3(b) and 4(a)–4(b).

Length $L_2$ of the protector 6: 16.5 mm

Nominal diameter $D_1$ of the mounting threaded portion 3a: M12×P1.25 (FIG. 1 thus far)

Length $L_3$ of the protrusion from the front-end surface of the main metal fitting 3 of the ceramic element 2: 5 mm Distance $L_4$ from the front-end surface of the first cylindrical portion 6b to the inner bottom surface of the second cylindrical portion 6a: less than 5 mm If the distance $L_4$ is in excess of 5 mm, the response might be deteriorated.

Length Ls of the tapering portion 6t: $D_6<L_5$ (3.5 mm)

If this length $L_5$ is outside the range, the response of the sensor 1 is more affected by the direction of the gas stream.

Tapering angle θ of the tapering portion 6t: less than 80° (45°)

The angle θ formed between the axis O of the first cylindrical portion 6b and the outer surface of the tapering portion 6t in a cross section including the axis O is defined as the tapering angle.

Distance $L_6$ in the axial direction from the inner bottom surface of the second cylindrical portion 6a to the center of the second side gas inlets 63: $L_4<L_6<L_4+L_5$ (3 mm)

Distance $L_7$ from the base end of the protector to the first side gas inlet 60 on the side of the base end: $L_7<L_3$ (1.8 mm)

Distance $L_8$ from the base end of the protector to the first side gas inlet 61 at the side of the front end: $L_3<L_8$ (6.8 mm).

Let $D_2$ be the inside diameter of the second cylindrical portion 6a. Let $D_3$ be the outside diameter of the first cylindrical portion 6b. $D_2-D_3=0.5$ to 10 mm (1.9 mm). If $D_2-D_3$ is less than 0.5 mm, flow of gas from the second side gas inlets 63 to the second side gas outlet 64 would be impeded, thus deteriorating the detection response. If the difference exceeds 10 mm, the negative pressure produces no longer desired result.

Inside diameter $D_4$ of the second side gas outlet 64: $D_5<D_4<D_3$ (4 mm). If $D_4$ becomes less than $D_5$, outflow of the gas from the second cylindrical portion 6a is impeded. This may impair the detection response.

Inside diameter $D_5$ of the first side gas outlet 62: 0.5 mm$<D_5<D_3$ (2 mm). If the inside diameter $D_5$ becomes less than 0.5 mm, outflow of the gas from the first cylindrical portion 6b is impeded. This may deteriorate the detection response.

Inside diameter $D_6$ of the second side gas inlets 63: 0.5 mm$<D_6<L_5$ (2 mm). If the inside diameter $D_6$ becomes less than 0.5 mm, inflow of the gas into the second cylindrical portion 6a is impeded. This may result in a deterioration of the detection response. If the inside diameter $D_6$ exceeds $L_5$, the response of the sensor 1 is more affected by the direction of the gas stream.

Inside diameter $D_7$ of the first side gas inlets 60 and 61: 0.5 mm$<D_7<4$ mm (1 mm). If the inside diameter $D_7$ becomes less than 0.5 mm, inflow of the gas into the first cylindrical portion 6b is impeded. This may deteriorate the detection response. If the inside diameter $D_7$ exceeds 4 mm, the response of the sensor 1 is more affected according to the direction of the gas stream.

The number $n_1$ of the second side gas inlets 63 formed in the circumferential direction: $n_1 \geq 2$. If the number $n_1$ is less than 2, inflow of the gas into the second cylindrical portion 6a is impeded. This may impair the detection response.

The number $n_2$ of the first side gas inlets 60 and 61 formed in the circumferential direction: $n_2 \geq 2$. If the number $n_2$ is less than 2, inflow of the gas into the first cylindrical portion 6b is impeded. This would degrade the detection response.

If the number of the gas inlets is excessive, the width between adjacent gas inlets becomes too small. This may lead to a decrease in the strength. The upper limits of the numbers $n_1$ and $n_2$ are set so as to prevent these inconveniences.

Figure 6A:
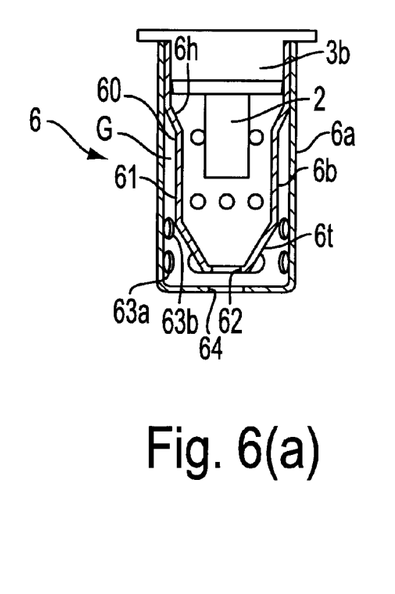

Modifications of the protector 6 are next described. FIG. 6(a) shows a modified example of the protector 6. This modified protector 6 has two arrays of second side gas inlets 63b and 63a in positions corresponding to the tapering portion 6t. This smoothens the flow of the gas along the outer surface of the tapering portion 6t. Therefore, the response is improved. In addition, it is less affected by the direction of the gas stream. In the structure shown in FIG. 6(a), circumferentially extending step portions 6h are formed to reduce the diameter of the first cylindrical portion 6b toward the front end. Thus, a gap G is formed with the second cylindrical portion 6a. The first cylindrical portion 6b has a base-end portion fitted over the reduced portion 3b of the main metal fitting 3. The second cylindrical portion 6a has a base-end portion that registers with its outer portion and is fitted in it. The first cylindrical portion 6b and the second cylindrical portion 6a are welded in their registering portions to the reduced portion 3b by a weldment not shown in the drawing.

Figure 6B:
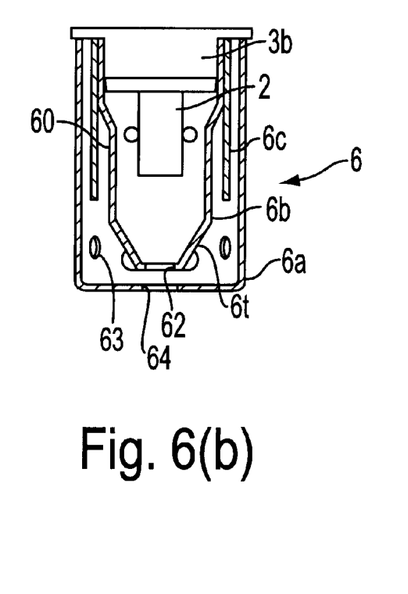

FIG. 6(b) shows a triple structure. That is, a third cylindrical portion 6c is formed between the first cylindrical portion 6b and the second cylindrical portion 6a and covers one array of first side gas inlets 60 on the side of the base end. This further suppresses intrusion of water droplets, oil, and contaminants into the first cylindrical portion 6b.

Figure 6C:
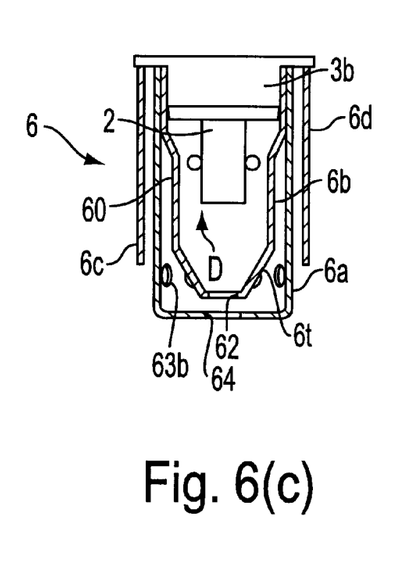

In FIG. 6(c), a third cylindrical portion 6c is located outside the second cylindrical portion 6a and covers the portion of the second cylindrical portion 6a at the side of the base end, but does not cover the second side gas inlets 63. If the gas flow rate increases rapidly, temperature drop of the detection portion D can be prevented more effectively.

Figure 6D:
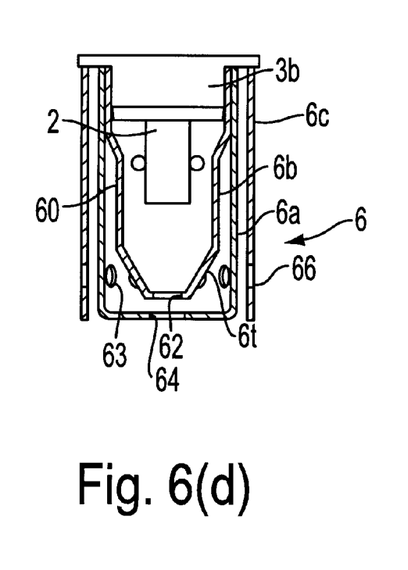

In FIG. 6(d), a third cylindrical portion 6c extends to the positions of the second side gas inlets 63. A third side gas inlet 66 is formed in the corresponding position. This further suppresses intrusion of water droplets, oil, and contaminants into the first cylindrical portion 6b.

Figure 7A:
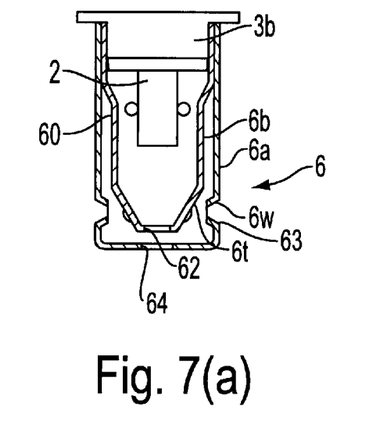

In FIG. 7(a), an airflow guide 6w is formed along the fringes of the second side gas inlets 63 and protrudes inwardly from the inner surface of the second cylindrical portion 6a. This reduces disturbance of the flow of exhaust gas going toward the tapering portion 6t. Hence, the response of the sensor 1 is less affected by the direction of the gas flow. That is, the advantage of the present invention is enhanced further.

Figure 7B:
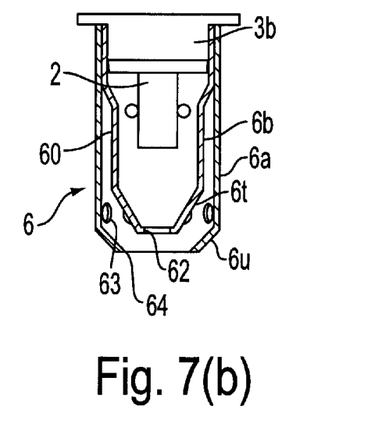

In FIG. 7(b), a tapering portion 6u is added at a side of the front end of the second cylindrical portion 6a. Consequently, the gas introduced in the protector 6 is sucked more effectively. Hence, the response of the sensor 1 is less affected by the direction of the gas stream. In this way, the advantage of the invention is enhanced further.

Figure 7C:
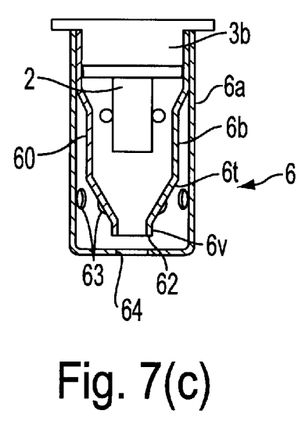
Figure 7D:
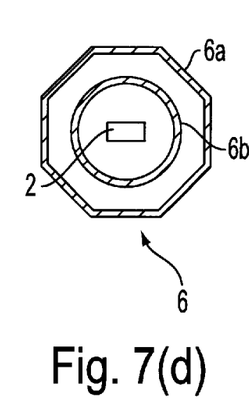

In FIG. 7(c), a cylindrical straight portion 6v is added at a side of the front end of the tapering portion 6t of the first cylindrical portion 6b. The second cylindrical portion 6a may have a polygonal horizontal cross section as shown in FIG. 7(d).

Figure 7E:
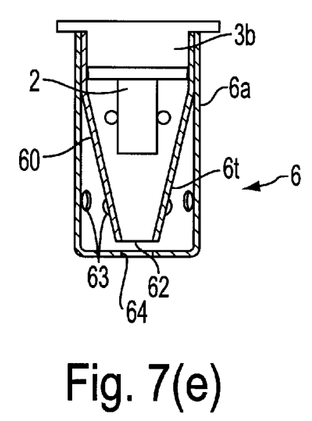
Figure 7F:
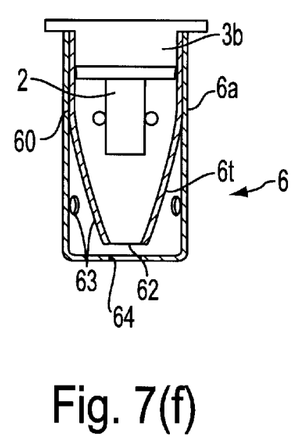

As shown in FIGS. 7(e) and 7(f), almost all of the first cylindrical portion 6b may be as a tapering portion 6t having a recessed outer surface. As shown in FIG. 7(e), the cross section may be almost straight. In this case, the contour of the tapering portion 6t assumes the form of a truncated cone. As shown in FIG. 7(f), the tapering portion 6t may be curved and outwardly protrude. In this case, the tapering portion 6t has a spindle-shaped contour.

Figure 7G:
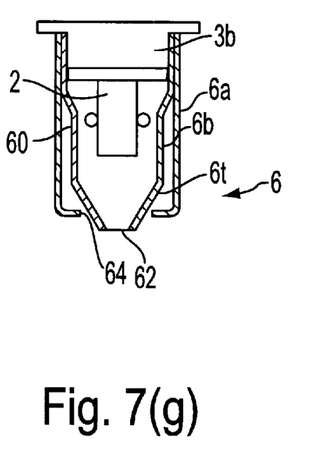

As shown in FIG. 7(g), the tapering portion 6t may have a front-end portion protruding beyond the second side gas outlet 64 (opening at the side of the front end). In this case, the inner fringes of the opening in the second side gas outlet 64 are located opposite to the outer surface of the tapering portion 6t.

FIGS. 8(a)–8(d) show a further example of modification of the protector. The second side gas inlets 63 and the first side gas inlets 60 have been modified as follows. The second side gas inlets 63 form a break 6a2 in the sidewall portion of the second cylindrical portion 6a. The crescent break 6a2 is curved or so shaped that it changes direction from one base end portion to the outer base end portion by its direction change portion 6a1. A claw-like portion 6a3 formed inside the break 6a2 is bent radially inwardly to form a crescent break. Exhaust gas EG introduced into the protector 6 from the second side gas inlets 63 flows along the outer surface of the reduced portion 6t of the first cylindrical portion 6b from the base end side toward the front end and then flows out from the second side gas outlet 64. At this time, the flow of the exhaust gas EG is made to circulate along the sidewall portion of the second cylindrical portion 6a by the claw-like portion 6a3 bent radially inwardly. This increases the flow velocity of the gas along the reduced portion 6t and so the negative pressure produced in the first side gas outlet 62 can be increased further. As a result, the rate at which the exhaust gas EG is sucked from the first side gas inlets 60 and 61 and hence the exchange rate of the exhaust gas EG inside the first cylindrical portion 6b is enhanced. The detection response or output response to concentration variations is improved further. The claw-like portion 6a3 overlaps the second side gas inlets 63 like a flap (see FIG. 8(b)). This suppresses intrusion of water droplets, oil droplets, and so on into the protector 6. Consequently, the detection portion D is protected well.

Figure 8A:
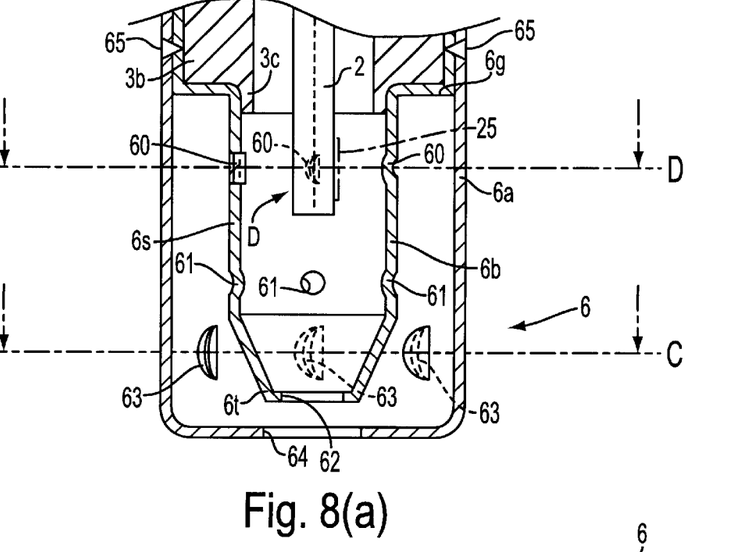
Figure 8B:
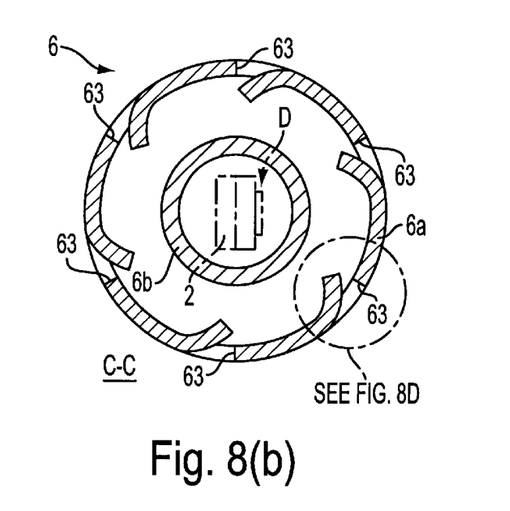
Figure 8C:
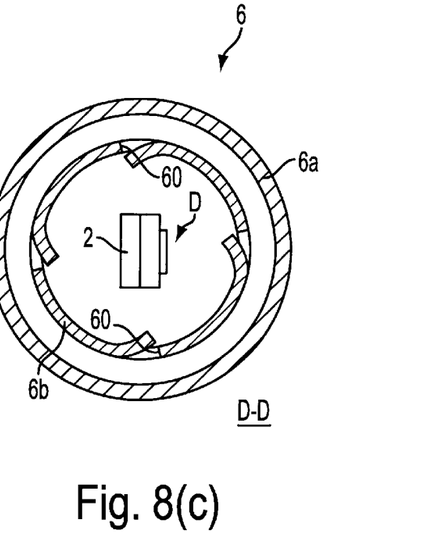
Figure 8D:
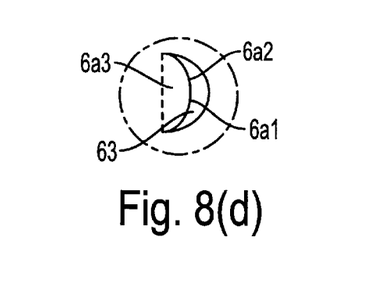

On the other hand, the holes 60 of the set of the first side gas inlets 60 and 61 located opposite to the detection portion D are formed by forming crescent breaks 6b2 in the sidewall portion of the first cylindrical portion 6b. The crescent breaks 6b2 are curved or so shaped that they change direction from one base end portion to the other base end portion by their direction change portion 6b1. Claw-like portions 6b3 formed inside the breaks 6b2 are radially inwardly bent, thus forming the holes 60. The inside of the first cylindrical portion 6b is sucked by the negative pressure generated in the first side gas outlet 62. The claw-like portions 6b3 bent radially inwardly make the flow of the exhaust gas EG to circulate along the sidewall portion of the first cylindrical portion 6b. The gas is sucked almost isotropically. As a result, circulating flow of the exhaust gas EG that is uniform around the axis of the protector 6 is created. Uniform response or output is derived. The claw-like portions 6b3 overlap the first side gas inlets 60 like flaps. This suppresses intrusion of water droplets, oil droplets, and so on into the first cylindrical portion 6b. The detection portion D is protected well.

The shapes of the breaks 6a2 and 6b2 can be modified appropriately. For example, they can be shaped into a U-shaped form. Furthermore, the number of the breaks 6a2 and 6b2, the positions of the bending lines, the bending directions, and so on can be modified.

The structure of the sensor in accordance with the present invention described thus far can be applied to gas sensors other than oxygen sensors, e.g., HC sensors and NOx sensors.

While the invention has been described in detail and with reference to specific embodiments thereof, it will be apparent to one skilled in the art that various changes and modifications can be made therein without departing from the spirit and scope thereof.

What is claimed is:

1. A gas sensor comprising:

a detection element having a front-end portion;

a detection portion formed at the front-end portion of the detection element; and a protector that covers the detection portion;

wherein said protector comprises a first portion having a first sidewall and a second portion having a second sidewall disposed outside said first portion, said first sidewall having an axial front end and a tapering portion, said tapering portion being formed from the axial front end of said first sidewall, said first portion having a front-end surface provided with a first gas outlet, said second portion having a front-end surface provided with a second gas outlet, and wherein at least one gas inlet is formed in the sidewall of said second portion opposite said tapering portion, and plural gas inlets are formed in the sidewall of said first portion.

2. The gas sensor of claim 1, wherein (a) said gas inlets formed in the sidewall of said first portion are circumferentially spaced from each other at given intervals, (b) said gas inlets formed in the sidewall of said first portion comprise two sets of holes axially spaced from each other, (c) the holes of one set of said two sets of holes are located opposite said detection portion, and (d) the holes of the other set are located forward of the front end of said detection portion.

3. The gas sensor of claim 2, wherein the holes of the set of gas inlets formed in the sidewall of said first portion located opposite to said detection portion are formed by forming curved breaks in the sidewall of said first portion so as to form claw-shaped portions inside the breaks and by bending the claw-shaped portions radially inwardly.

4. The gas sensor of claim 1, wherein said second gas outlet is larger than said first gas outlet.

5. The gas sensor of claim 1, wherein said gas inlets formed in the sidewall of said second portion are formed by forming curved breaks in the sidewall of said second portion so as to form claw-shaped portions inside the breaks and by bending the claw-shaped portions radially inwardly.

6. A gas sensor according to claim 1, wherein said tapering portion of said first portion is in the form of a truncated cone coupled to the front end of a cylindrical body.

7. A gas sensor according to claim 1, wherein a gas-sensitive surface is formed in a part of the outer peripheral surface of said detection portion.

8. A gas sensor according to claim 7, wherein (a) said detection portion is an oxygen detection portion comprising an oxygen concentration cell and a laminar heater, (b) said oxygen concentration cell has a board-like layer of an oxygen ion conductive solid electrolyte, a first porous electrode at one side of said layer and acting as a detection electrode, and a second porous electrode located on an opposite side of said first porous electrode and acting as an oxygen reference electrode, (c) said laminar heater is mounted on said second porous electrode, and (d) said first porous electrode acting as the detection electrode forms said gas-sensitive surface.

9. The gas sensor according to claim 1, wherein said tapering portion is located forward of said detection portion, said plural gas inlets formed in the sidewall of the first portion include gas inlets arranged opposite said detection portion, and said protector comprising plural gas inlets formed in the sidewall of said second portion opposite said tapering portion.

10. The gas sensor according to claim 1, comprising two arrays of gas inlets formed in the sidewall of said second portion opposite said tapering portion.

11. The gas sensor according to claim 1, wherein said protector comprises a third portion formed between the first portion and the second portion.

12. The gas sensor according to claim 1, wherein said protector comprises a third portion located outside the second portion, said third portion covering a part of the second portion but not covering the gas inlets formed in the sidewall of the second portion.

13. The gas sensor according to claim 1, wherein said protector comprises a third portion located outside the second portion, said third portion covering the gas inlets formed in the sidewall of the second portion.

14. The gas sensor according to claim 1, comprising an airflow guide formed along an edge of said gas inlet formed in the sidewall of said second portion.

15. The gas sensor according to claim 1, comprising a tapering portion formed at a side of the front end of the second portion.

16. The gas sensor according to claim 1, comprising a straight portion formed at a side of the front end of the tapering portion of said first portion.

17. The gas sensor according to claim 1, wherein the tapering portion constitutes substantially all of said first portion.

18. The gas sensor according to claim 17, wherein the tapering portion of said first portion is curved and protrudes outwardly.

19. The gas sensor according to claim 1, producing a gas stream when measurement gas introduced in the protector from the gas inlet formed in the sidewall of the second portion flows along an outer surface of said tapering portion and flows out of the second gas outlet, said gas stream generating a negative pressure in the first gas outlet, evacuating an inside of said first portion and drawing in measurement gas from the gas inlets formed in the sidewall of the first portion.

20. The gas sensor according to claim 19, isotropically drawing in measurement gas from the gas inlets formed in the sidewall of the first portion.

* * * * *